United States Patent
Berch et al.

(10) Patent No.: US 11,607,485 B2
(45) Date of Patent: Mar. 21, 2023

(54) SYSTEMS FOR ELIMINATING AND/OR REDUCING AEROSOL EMISSIONS FROM A HEATER/COOLER

(71) Applicant: Sorin Group Italia S.r.l., Milan (IT)

(72) Inventors: Stephen W. Berch, Arvada, CO (US); Thierry Dupoux, Sceaux (FR); Elisa Maculan, Gallarate (IT); Giampaolo Simonini, Reggio nell'Emilia (IT)

(73) Assignee: Sorin Group Italia S.r.l., Milan (IT)

( * ) Notice: Subject to any disclaimer, the term of this patent is extended or adjusted under 35 U.S.C. 154(b) by 275 days.

(21) Appl. No.: 16/304,460

(22) PCT Filed: Sep. 14, 2016

(86) PCT No.: PCT/IB2016/055470
§ 371 (c)(1),
(2) Date: Nov. 26, 2018

(87) PCT Pub. No.: WO2018/051165
PCT Pub. Date: Mar. 22, 2018

(65) Prior Publication Data
US 2019/0192748 A1    Jun. 27, 2019

(51) Int. Cl.
*A61M 1/00* (2006.01)
*A61L 9/16* (2006.01)
(Continued)

(52) U.S. Cl.
CPC .............. *A61M 1/784* (2021.05); *A61L 9/16* (2013.01); *A61F 7/0097* (2013.01);
(Continued)

(58) Field of Classification Search
CPC .. A61M 1/0052; A61M 1/3666; A61M 1/369; A61M 1/1698; A61M 19/00;
(Continued)

(56) References Cited

U.S. PATENT DOCUMENTS

| 5,039,494 A | 8/1991 | Martin et al. |
| 6,585,791 B1 | 7/2003 | Garito et al. |

(Continued)

FOREIGN PATENT DOCUMENTS

| JP | 55-072404 | 5/1980 |
| JP | 56-172346 U | 12/1981 |

(Continued)

OTHER PUBLICATIONS

"Frequently Asked Questions regarding the 3TFSN Update on CardiacSurgery *Mycobacterium* Risks-Sorin Heater—Cooler Device Upgrade/Design Modification", May 1, 2017 (May 1, 2017), XP055379848, Retrieved from the Internet: URL:http://www.livanova.sorin.com/file/download-7958.action [retrieved on Jun. 8, 2017] p. 5.

(Continued)

*Primary Examiner* — Jason M Greene
(74) *Attorney, Agent, or Firm* — Seager, Tufte & Wickhem LLP (57) ABSTRACT

A system including tubing and a filter configured to be fluidly coupled to a vacuum source and to a heater/cooler unit by the tubing. The filter includes a filter container having negative air pressure in the filter container provided by the vacuum source to pull aerosol from the heater/cooler unit into the filter container and eliminate and/or reduce the aerosol emitted from the heater/cooler unit.

23 Claims, 7 Drawing Sheets

(51) Int. Cl.
*A61M 1/16* (2006.01)
*A61M 1/36* (2006.01)
*A61F 7/00* (2006.01)
*A61M 19/00* (2006.01)

(52) U.S. Cl.
CPC ........ *A61L 2209/11* (2013.01); *A61L 2209/14* (2013.01); *A61M 1/1698* (2013.01); *A61M 1/369* (2013.01); *A61M 1/3666* (2013.01); *A61M 19/00* (2013.01); *A61M 2205/366* (2013.01); *A61M 2205/7518* (2013.01)

(58) Field of Classification Search
CPC ..... A61M 2205/366; A61M 2205/7518; A61L 9/16; A61L 2209/11; A61L 2209/14; A61F 7/0097
See application file for complete search history.

(56) References Cited

U.S. PATENT DOCUMENTS

| | | | |
|---|---|---|---|
| 9,259,523 | B2 | 2/2016 | Schreyer et al. |
| 2002/0055725 | A1 | 5/2002 | Verkaart et al. |
| 2004/0186339 | A1* | 9/2004 | Galloway ................ A61L 9/16 |
| | | | 588/316 |
| 2009/0326488 | A1* | 12/2009 | Budig .................. A61M 1/784 |
| | | | 604/319 |

FOREIGN PATENT DOCUMENTS

| | | |
|---|---|---|
| JP | 08-243322 A | 9/1996 |
| JP | 11-513596 A | 11/1999 |
| JP | 2002-303436 A | 10/2002 |
| JP | 2007-195996 A | 8/2007 |

OTHER PUBLICATIONS

International Search Report and Written Opinion received for PCT Patent Application No. PCT/IB2016/055470, dated Jul. 26, 2017, 20 pages.

Peter W. Schreiber et al.: "Reemergence of *Mycobacterium chimaera* in Heater-Cooler Units despite Intensified Cleaning and Disinfection Protocol", Emerging Infectious Diseases, vol. 22, No. 10, Oct. 1, 2016 (Oct. 1, 2016), pp. 1830-1833.

Rami Sommerstein et al.: "Transmission of *Mycobacterium chimaera* from Heater-Cooler Units during Cardiac Surgery despite an Ultraclean Air Ventilation System", Emerging Infectious Diseases, vol. 22, No. 6, Jun. 1, 2016 (Jun. 1, 2016), pp. 1008-1013.

Rami Sommerstein: "Cardiac surgery, nosocomial infection, and the built environment", Journal of Hospital Infection, Elsevier, Amsterdam, NL, vol. 93, No. 3, May 10, 2016 (May 10, 2016), pp. 240-241.

Richard Kuehl et al: "Not all heater-cooler units are equal—different risk for environmental contamination with *Mycobacterium chimaera* during open heart surgery", Apr. 25, 2017 (Apr. 25, 2017), XP055379969, Retrieved from the Internet: URL:https://www.escmid.org/escmid publications/escmid elibrary/material/?mid=52527 [retrieved on Jun. 9, 2017].

* cited by examiner

```
┌─────────────────────────────────────────────────┐
│  FLUIDICALLY COUPLING A FILTER TO A VACUUM SOURCE │──── 200
│        AND TO A HEATER/COOLER UNIT                │
└─────────────────────────────────────────────────┘
                        │
┌─────────────────────────────────────────────────┐
│ ACTIVATING THE VACUUM SOURCE TO PROVIDE NEGATIVE │
│ AIR PRESSURE IN THE FILTER AND PULL AEROSOL FROM │──── 202
│           THE HEATER/COOLER UNIT                  │
└─────────────────────────────────────────────────┘
```

SYSTEMS FOR ELIMINATING AND/OR REDUCING AEROSOL EMISSIONS FROM A HEATER/COOLER

CROSS-REFERENCE TO RELATED APPLICATION

This application is a national stage application of PCT/IB2016/055470, filed Sep. 14, 2016, which is herein incorporated by reference in its entirety.

TECHNICAL FIELD

The present disclosure relates to medical devices and methods for preventing infections. More specifically, the disclosure relates to medical devices and methods for eliminating and/or reducing aerosol emitted from a heater/cooler unit in an operating room environment for cardiac surgery.

BACKGROUND

Heater/cooler units or devices are important tools in surgeries involving the heart, lungs, and other cardiothoracic surgeries. Heater/cooler units can be used to warm or cool a patient, the patient's blood, and/or other fluids used during surgery. Heater/cooler units include tanks that provide temperature-controlled water to external heat exchangers or to warming/cooling blankets through closed water circuits. For example, in cardiopulmonary bypass (CPB) surgeries, a heater/cooler unit can be used with a heart-lung machine featuring separate temperature control for extracorporeal perfusions. The heater/cooler water or fluid circuits are used for heating and cooling blood in the oxygenator, hypothermia blankets, and cardioplegic solutions.

It is often recommended that heater/cooler units be cleaned on a regular basis, such as every two weeks. Cleaning a heater/cooler unit may include completely draining the fluid tanks and rinsing the water circuits with sanitizing agents. If the heater/cooler is not cleaned regularly, micro-organisms may grow inside the unit. These micro-organisms may exit the heater/cooler unit, be dispersed in the operating room, and reach the surgical operating theatre, potentially causing infections in the patient.

SUMMARY

A first example system of the disclosure includes a filter configured to be fluidly coupled by tubing to a vacuum source and to a tank or an internal space of a heater/cooler unit by the tubing. The filter includes a filter container having negative air pressure therein provided by the vacuum source to suction aerosol from the heater/cooler unit internal space (or tank) into the filter container and eliminate or reduce the aerosol emitted from the heater/cooler unit. The aerosol is segregated from the heater/cooler unit and prevented from being dispersed in the operating theatre.

A second example system of the disclosure includes tubing including a first tube and a second tube, a vacuum source, and a filter fluidly coupled to the vacuum source by the first tube and an internal space in a heater/cooler unit by the second tube. The vacuum source provides negative air pressure to the filter to suction aerosol from the heater/cooler unit.

A third example system of the disclosure includes tubing and a filter configured to be fluidly coupled to a vacuum source and to an internal space (or tank) of a heater/cooler unit by the tubing, such that the filter receives negative air pressure from the vacuum source to suction aerosol from the heater/cooler unit into the filter. At least one of the tubing and the filter is disposable to reduce contamination and prevent build-up of contamination.

A fourth example system of the disclosure includes a disposable unit to be fluidly coupled to a vacuum source and to an internal space of a heater/cooler unit, the disposable unit having an aerosol filter and tubing to couple the disposable unit to the vacuum source and to the internal space of the heater/cooler unit.

A first example method of the disclosure includes eliminating or reducing aerosol emitted from a heater/cooler unit by fluidly coupling a filter to a vacuum source and to either an internal space or a tank of the heater/cooler unit by tubing and activating the vacuum source for a time to provide negative air pressure in the filter and suction the aerosol from the heater/cooler unit into the filter. A sensor may be provided to sense the presence of aerosols, or conditions likely to result in the production of aerosols, in the heater/cooler unit. The sensor may be used to activate or deactivate the vacuum source.

A second example method of the disclosure includes reducing aerosol emitted from a heater/cooler unit operable during a surgical procedure on a patient, the heater/cooler unit comprising a heater, an internal space comprising a fluid tank, and an overflow port, by connecting a filter to a vacuum source and the overflow port of the heater/cooler unit by tubing, activating the vacuum source for at least a limited time during at least a portion of an operation of the heater to provide negative air pressure in the filter and suction aerosol from the internal space (or the tank) of the heater/cooler unit into the filter, disconnecting the filter and tubing from the vacuum source and the overflow port after completion of the surgical procedure, and disposing of the filter and tubing While multiple embodiments are disclosed, still other embodiments of the present disclosure will become apparent to those skilled in the art from the following detailed description, which shows and describes illustrative embodiments of the disclosure. Accordingly, the drawings and detailed description are illustrative in nature and not restrictive.

While the disclosure is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

DETAILED DESCRIPTION

Figure 1:
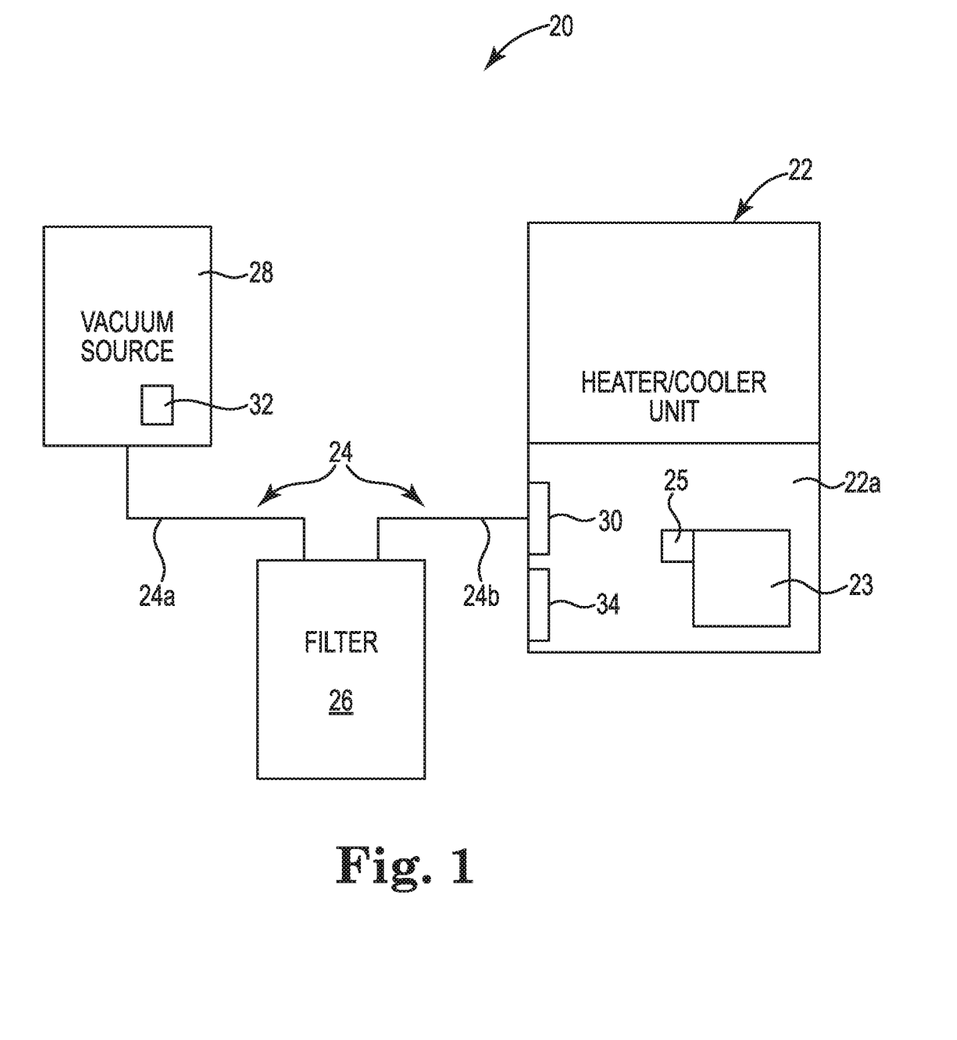
FIG. 1 is a diagram illustrating a system for eliminating and/or reducing the aerosol emitted from a heater/cooler unit, according to embodiments of the disclosure.

FIG. 1 is a diagram illustrating a system 20 for reducing the aerosol emitted from a heater/cooler unit 22 having an internal space 22a, according to various embodiments of the disclosure. A variety of heater/cooler units 22 are well known to the skilled artisan. Heater/cooler units generally include an internal space 22a having one or more fluid tanks 23 or containers coupled to a heating and/or cooling source. Internal space 22a includes any space in the heater/cooler unit 22 within which an aerosol may be present. In some embodiments, internal space 22a includes any space within the outer surfaces of the heater/cooler unit 22. In some embodiments, internal space 22a includes an internal space within the one or more fluid tanks 23. Additionally, heater/cooler units 22 typically include a control system for controlling the desired fluid temperature and flow of the fluid from the tank 23 (or tanks) to the desired component or location. Most typically, the fluid used in the heater/cooler unit 22 is water, often with an added disinfectant. Additional details of heater/cooler units are described in U.S. Pat. No. 9,259,523, which is hereby incorporated by reference.

The system 20 further includes tubing 24 and a filter unit 26. The filter unit 26 is fluidly coupled to the heater/cooler unit 22 and to a vacuum source 28 by the tubing 24. In some embodiments, the tubing 24 is configured to be detachably coupled to at least one of the filter unit 26, the heater/cooler unit 22, and the vacuum source 28. In some embodiments, the filter unit 26 is configured to be detachably coupled to at least one of the tubing 24, the heater/cooler unit 22, and the vacuum source 28. In some embodiments, at least one of the tubing 24 and the filter unit 26 is disposable, such that contamination from the disposable part(s) is discarded and build-up of contamination is prevented. In some embodiments, both the tubing and the filter unit are disposable, either as individual items or together as part of a single disposable unit. In still further embodiments, a sterile disposable unit having an aerosol filter unit and tubing may be provided in a sealed container.

Referring again to FIG. 1, the filter unit 26 is coupled to the vacuum source 28 by a first tube 24a of the tubing 24 and to an internal space 22a of the heater/cooler unit 22 by a second tube 24b of the tubing 24. In some embodiments, the vacuum source 28 is a house vacuum provided by a medical facility, such as through a wall vacuum socket in an operating room. In some embodiments, the vacuum source 28 is a non-disposable vacuum source that can be provided with the system 20 including the tubing 24 and the filter unit 26. In some embodiments, the vacuum source 28 is a disposable vacuum unit that is provided as a part of a disposable unit including the filter unit 26 and the tubing 24. In some embodiments, the second tube 24b is coupled to an existing overflow port 30 on the heater/cooler unit 28, which is fluidly coupled to the internal space 22a of the heater/cooler unit 28. The existing overflow port 30 is provided for fluid overflow of one or more of the tanks 23 in the internal space 22a of heater/cooler unit 22. Connecting the second tube 24b to an existing overflow port 30 enables the tubing 24 and the filter unit 26 to be retrofit to an existing heater/cooler unit 22. In some embodiments, the tank 23 is closed, such that fluid in the tank 23 is not open to the internal space 22a above the tank 23, instead the tank 23 is enclosed such as with a lid, and the overflow port 30 is coupled directly to the tank 23. In other embodiments, the tank 23 or fluid in the tank 23 is open to the internal space 22a above the tank 23, and the overflow port 30 is coupled to the internal space 22a above the tank 23. In some embodiments, the second tube 24b is coupled to the heater/cooler unit 28 and fluidly coupled to the internal space 22a of the heater/cooler unit 28, with or without being coupled to an overflow port, such as the overflow port 30. In some embodiments, the tank 23 is closed, such that fluid in the tank 23 is not open to the internal space 22a above the tank 23, instead the tank 23 is enclosed such as with a lid, and the second tube 24b is coupled directly to the tank 23, with or without being coupled to an overflow port, such as the overflow port 30. In other embodiments, the tank 23 or fluid in the tank 23 is open to the internal space 22a above the tank 23, and the second tube 24b is coupled to the internal space 22a above the tank 23, with or without being coupled to an overflow port, such as the overflow port 30.

In some embodiments, a disposable aerosol removal kits for coupling to an existing overflow port 30 on a heater/cooler unit 22 may include a filter unit 26 and tubing 24. Optionally, a disposable vacuum element may also be included in the disposable kit. The disposable kit may be provided as a sterile unit in a sealed container.

In operation, the vacuum source 28 is activated to provide a vacuum or a negative air pressure relative to the external air pressure to the filter unit 26. In some embodiments, the vacuum source 28 is manually activated. In some embodiments, the vacuum source 28 includes an electronic control circuit 32 that activates the vacuum source 28 for a limited duration to remove the aerosol from the heater/cooler unit 22. In some embodiments, the vacuum source 28 includes an electronic control circuit 32 that activates the vacuum source 28 for at least 10 minutes to remove the aerosol from the heater/cooler unit 22. In some embodiments, the vacuum source 28 includes an electronic control circuit 32 that activates the vacuum source 28 whenever the heater/cooler unit 22 is activated to remove the aerosol from the internal space 22a of the heater/cooler unit 22. In some embodiments, the vacuum source 28 is turned on before the heater/cooler unit 22 is turned on. In some embodiments, the vacuum source 28 is turned on at the same time the heater/cooler unit 22 is turned on.

In some embodiments, the heater/cooler unit 22 includes a pressure sensor 25 to determine the pressure in at least one of the internal space 22a and the one or more tanks 23. In some embodiments, the pressure sensor 25 is communicatively coupled to the electronic control circuit 32, such as by wire or wirelessly. In some embodiments, electronic control circuit 32 activates the vacuum source 28 based on a signal from the pressure sensor 25 indicating that the pressure equals or exceeds a pressure where aerosols may escape from the heater/cooler unit 22 and into the environment. In some embodiments, electronic control circuit 32 activates the vacuum source 28 based on a signal from the pressure sensor 25 indicating that the pressure equals or exceeds the current ambient pressure, also referred to as zero herein. In some embodiments, electronic control circuit 32 activates the vacuum source 28 based on a signal from the pressure sensor 25 indicating that the pressure equals or exceeds the current atmospheric pressure. In some embodiments, electronic control circuit 32 activates the vacuum source 28 based on a signal from the pressure sensor 25 indicating the pressure equals or exceeds a pressure threshold. In some embodiments, the pressure threshold is a factory preset threshold. In some embodiments, the pressure threshold is set by an operator and/or the electronic control circuit 32. In some embodiments, the pressure threshold is zero or the current ambient pressure. In some embodiments, electronic control circuit 32 activates the vacuum source 28 for a predetermined duration. In some embodiments, the electronic control circuit 32 activates the vacuum source 28 until the signal from the pressure sensor 25 indicates the pressure has been reduced, such that the danger of aerosols escaping has been eliminated. In some embodiments, the electronic control circuit 32 activates the vacuum source 28 until the signal from the pressure sensor 25 indicates the pressure is below the pressure threshold. In some embodiments, the electronic control circuit 32 activates the vacuum source 28 in response to the signal from the pressure sensor 25 indicating the pressure is a non-negative pressure, such as equal to or greater than the current ambient pressure. In some embodiments, the electronic control circuit 32 activates the vacuum source 28 based on the signal from the pressure sensor 25 to maintain a negative pressure, such as less than the current ambient pressure, in at least one of the internal space 22a and the one or more tanks 23 to prevent aerosols from escaping from the heater/cooler unit 22 and into the surrounding environment.

In some embodiments, the heater/cooler unit 22 includes a sensor 34 to determine an aerosols concentration in the internal space 22a of the heater/cooler unit. In some embodiments, electronic control circuit 32 activates the vacuum source 28 based on a signal from sensor 34 indicating that any aerosols have been detected. In some embodiments, electronic control circuit 32 activates the vacuum source 28 based on a signal from sensor 34 indicating an aerosols concentration exceeding an aerosol concentration threshold. In some embodiments, the aerosol concentration threshold is a factory preset threshold. In some embodiments, the aerosol concentration threshold is set by an operator. In some embodiments, electronic control circuit 32 activates the vacuum source 28 for a predetermined duration. In some embodiments, the electronic control circuit 32 activates the vacuum source 28 until the signal from sensor 34 indicates all aerosols have been eliminated. In some embodiments, the electronic control circuit 32 activates the vacuum source 28 until the signal from sensor 34 indicates an aerosols concentration below a threshold. In some embodiments, sensor 34 may be located outside the heater/cooler unit 22, such as in tubing 24b connecting heater/cooler 22 and filter unit 26.

The filter unit 26 includes a filter container or bottle and the negative air pressure is provided to the filter container to suction aerosol from the heater/cooler unit 22 into the filter container. This eliminates and/or reduces the amount of aerosol that escapes from the heater/cooler unit 22 and diffuses into the ambient air of the operating theatre. In some embodiments, the filter unit 26 includes an antibacterial filter element. In some embodiments, the filter unit 26 includes an antibacterial filter element that includes at least one of a hydrophobic filter element and a hydrophilic filter element. In some embodiments, systems of the present disclosure, such as system 20, are capable of substantially removing all aerosols and/or bacteria from the system, and prevent any aerosol or bacteria from entering the operating room environment. In some embodiments, systems of the present disclosure, such as system 20, reduce the aerosol emitted from the heater/cooler unit 22 by at least 95%.

Figure 2:
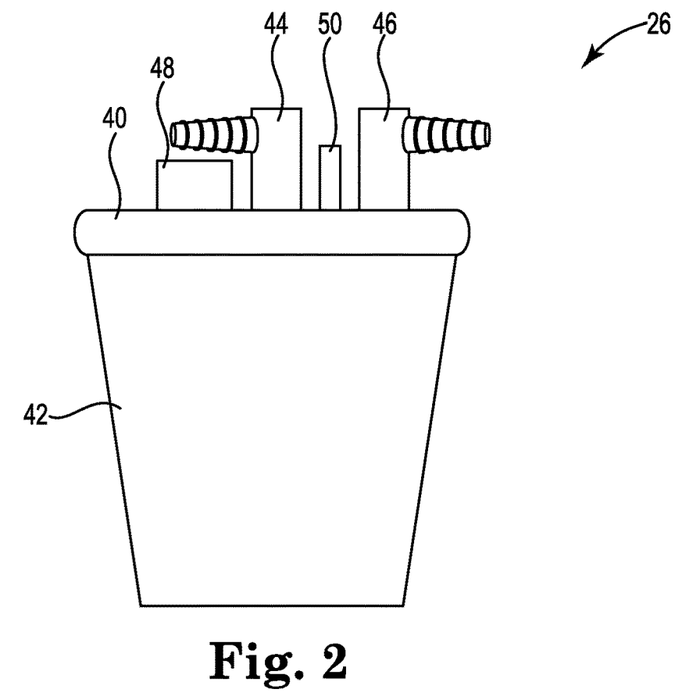
FIG. 2 is a diagram illustrating the filter of FIG. 1, according to embodiments of the disclosure.
Figure 3:
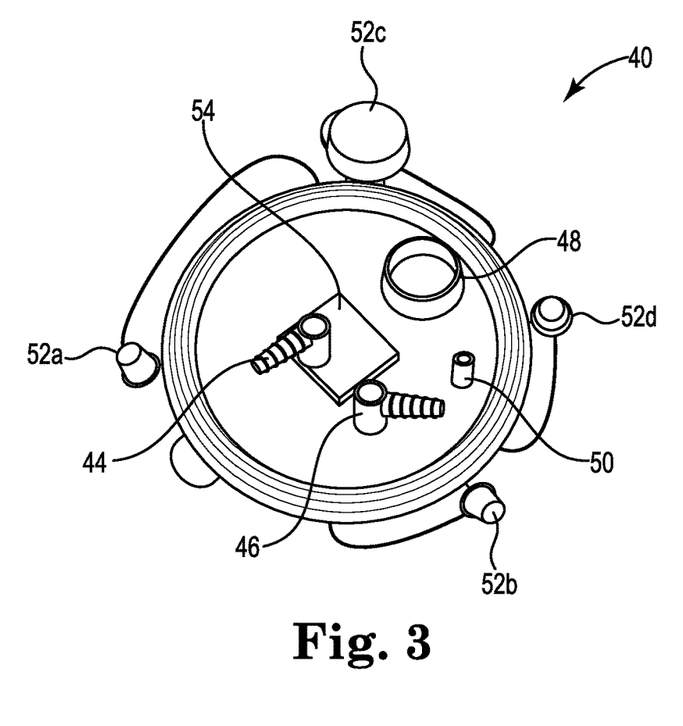
FIG. 3 is a diagram illustrating a top view of a filter cap, according to embodiments of the disclosure.
Figure 4:
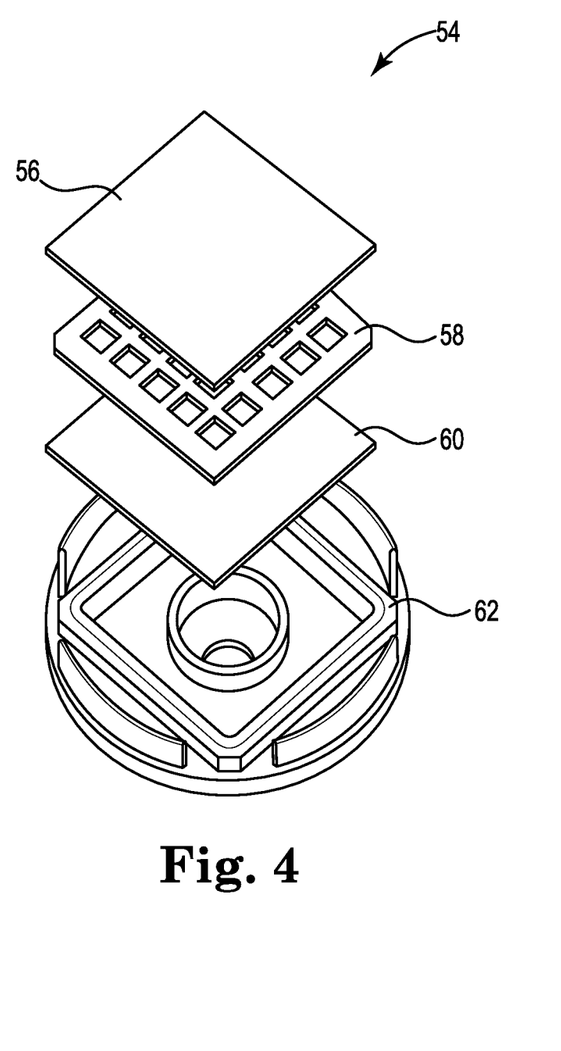
FIG. 4 is a diagram illustrating a hydrophobic filter, according to embodiments of the disclosure.

FIGS. 2-4 are diagrams illustrating the filter unit 26, according to various embodiments of the disclosure. The filter unit 26 receives and filters the aerosol received from the internal space (or the tank) of the heater/cooler unit 22. The filter unit 26 prevents contaminants or microorganisms, such as bacteria, from entering the vacuum source 28.

FIG. 2 is a diagram illustrating the filter unit 26, according to some embodiments of the disclosure. The filter unit 26 includes a filter cap 40 and a filter container 42. The filter cap 40 is or can be attached to the filter container 42 in an air tight connection to allow for creating a negative air pressure in the filter container 42. In some embodiments, the filter cap 40 is attached to the filter container 42 in an air tight connection to prevent captured aerosol from escaping into the ambient air of the operating theatre. In some embodiments, the filter cap 40 is detachably or removably attached to the filter container 42, for example, by a snap-fit engagement or a threaded connection. In some embodiments, the filter cap 40 is fixedly attached to the filter container 42, such that the filter cap 40 cannot be easily removed from the filter container 42. In some embodiments, the filter cap 40 is integrally formed with the filter container 42 and cannot be removed.

FIG. 3 is a diagram illustrating a top view of the filter cap 40, according to embodiments of the disclosure. The filter cap 40 includes a first connection 44 and a second connection 46 for connecting the tubing 24 to the filter cap 40. The first connection 44 is used to connect the filter cap 40 to the vacuum source 28, and the second connection 46 is used to connect the filter cap 40 to the heater/cooler unit 22. In other embodiments, the first connection 44 is used to connect the filter cap 40 to the heater/cooler unit 22, and the second connection 46 is used to connect the filter cap 40 to the vacuum source 28. In the embodiment of FIGS. 2 and 3, the first connection 44 and the second connection 46 are right angle or elbow connections. In other embodiments, however, one or both of the first and second connections 44 and 46 can be differently shaped connections, such as straight, vertical connections.

In one embodiment, the filter cap 40 also includes a pour spout 48, and a tandem port 50. The pour spout 48 is configured to be used for emptying the filter container 42 or connecting the filter unit 26 to a specimen collector. The tandem port 50 is configured to be used to connect multiple filters, such as a second filter unit (not shown), in series or parallel with filter unit 26, to collect and filter aerosol. In some embodiments, the filter cap 40 further includes attached port caps 52a and 52b for capping the first connection 44 and the second connection 46, respectively. In some embodiments, port cap 52c is provided for capping the pour spout 48, and port cap 52d is provided for capping the tandem port 50. The port caps 52a-52d can be used to eliminate cap loss and allow for quick and secure capping of the filter unit 26.

In some embodiments, the filter cap 40 includes an antibacterial filter element. In some embodiments, the filter cap 40 includes an antibacterial filter element that includes at least one of a hydrophobic filter element and a hydrophilic filter element. In some embodiments, the antibacterial filter element includes a hydrophobic filter element 54, attached below the first connection 44 and to the underside of the filter cap 40. The filter unit 26 filters the aerosol received from the heater/cooler unit 22 at or near the first connection 44, which is coupled to the vacuum source 28. The filter unit 26 captures contaminants in the hydrophobic filter element 54, and prevents contaminants, such as bacteria, from entering the vacuum source 28. In some embodiments, the filter unit 26 filters the aerosol received from the heater/cooler unit 22 at or near the second connection 46, which is coupled to the heater/cooler unit 22, to capture contaminants in the hydrophobic filter 54 and prevent contaminants, such as bacteria, from entering the filter container 42. In some embodiments, the filter unit 26 includes a hydrophobic filter 54 configured to filter up to 99.99 percent of aerosolized micro-organisms and particulate matter in the aerosol received from the heater/cooler unit 22. In some embodiments, the antibacterial filter element includes a hydrophilic filter element.

FIG. 4 is a diagram illustrating a hydrophobic filter element 54, according to various embodiments of the disclosure. The hydrophobic filter element 54 includes a hydrophobic filter stage 56, a breathing screen 58, a pre-filter stage 60, and a housing 62. The hydrophobic filter stage 56, breathing screen 58, and pre-filter stage 60 are housed in the housing 62, which protects these filter components from splash and foam. The breathing screen 58 separates the hydrophobic filter stage 56 from the pre-filter stage 60. In one embodiment, the hydrophobic filter stage 56 is configured to filter up to 99.99 percent of aerosolized micro-organisms and particulate matter. In some embodiments, the hydrophobic filter element 54 includes a hydrophobic shut-off filter that closes the suction port or stops vacuum flow when contacted by fluid, such as fluid suctioned into the container, and the breathing screen 58 separates the hydrophobic filter stage 56 from the pre-filter stage 60 to improve suction while reducing premature shut-off. In some embodiments the hydrophobic filter element 54 includes a hydrophobic shut-off filter that closes the suction port or stops vacuum flow when contacted by fluid, such as fluid suctioned into the container, and the pre-filter stage 60 protects the hydrophobic filter stage 56 from erroneous shut-off due to laser or electrocautery smoke.

In some embodiments, the hydrophobic filter stage 56 filters the aerosol received from the heater/cooler unit 22 at or near the first connection 44, which is coupled to the vacuum source 28. In some embodiments, the hydrophobic filter 56 filters the aerosol received from the heater/cooler unit 22 at or near the second connection 46, which is coupled to the heater/cooler unit 22. In still further embodiments, two hydrophobic filter stages 56 are provided, one at or near each of the first and second connections 44 and 46, respectively.

Figure 5:
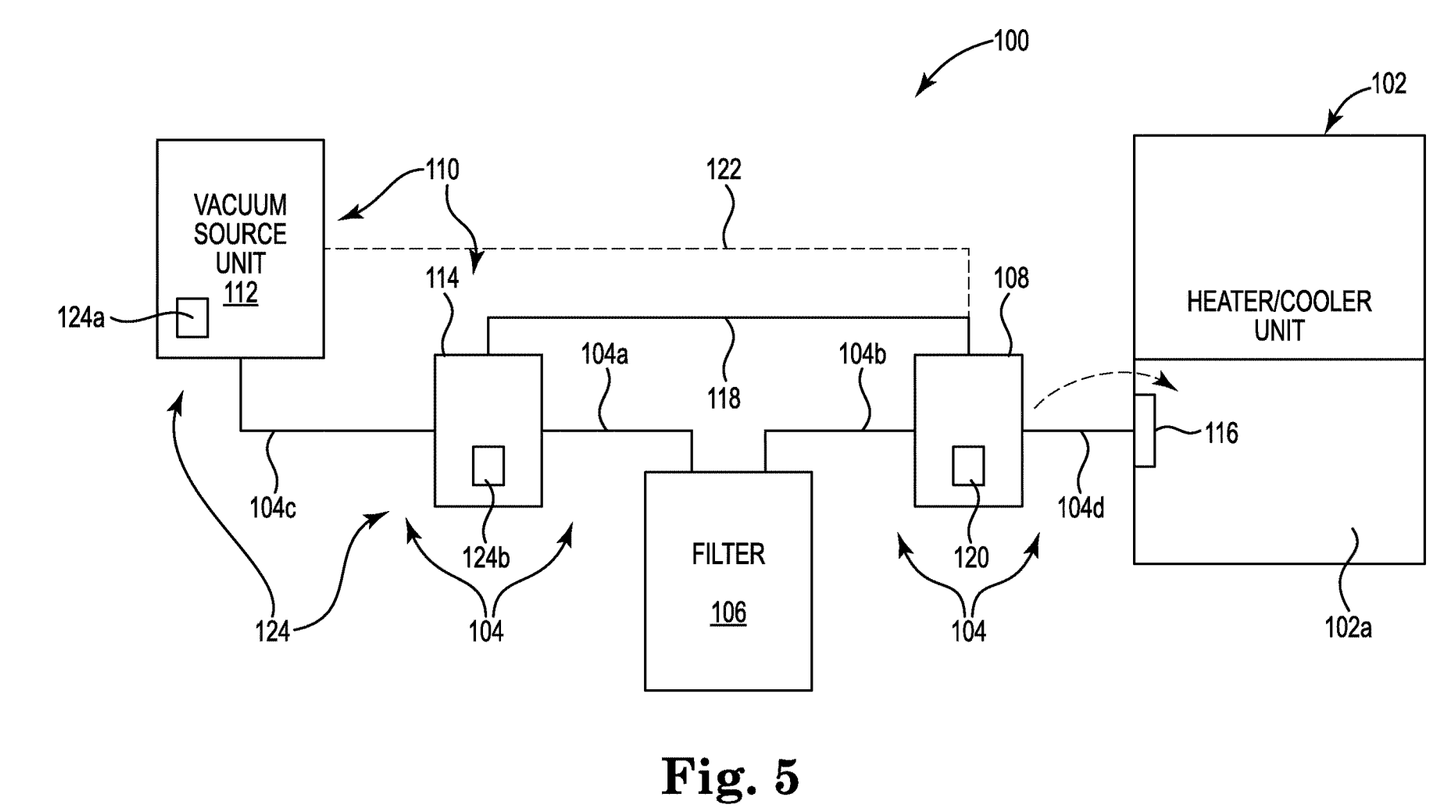
FIG. 5 is a diagram illustrating a system for eliminating and/or reducing the aerosol emitted from a heater/cooler unit, according to embodiments of the disclosure.

FIG. 5 is a diagram illustrating a system 100 for reducing the aerosol emitted from a heater/cooler unit 102 having an internal space 102a, according to some embodiments of the disclosure. The system 100 includes tubing 104, a filter 106, and a sensor 108. In some embodiments, the tubing 104 is similar to the tubing 24. In some embodiments, the filter 106 is similar to the filter unit 26. Also, in some embodiments, the heater/cooler unit 102 is similar to the heater/cooler unit 22.

Vacuum source 110 includes a vacuum source unit 112 and a vacuum valve 114 for providing a vacuum or negative air pressure relative to the external air pressure to the filter 106. In some embodiments, the vacuum source 110 including the vacuum source unit 112 includes the house vacuum of the medical facility. In some embodiments, the vacuum source unit 112 is a non-disposable vacuum source unit. In some embodiments, the vacuum source unit 112 is a disposable vacuum source unit that may be discarded.

The filter 106 is fluidly coupled to the vacuum valve 114 by the tubing 104 and to the sensor 108 by the tubing 104. The vacuum valve 114 is fluidly coupled to the vacuum source unit 112 by the tubing 104, and the sensor 108 is fluidly coupled to the internal space 102a (or the tank) of the heater/cooler unit 102 by the tubing 104. In some embodiments, the tubing 104 is configured to be detachably coupled to at least one of the filter 106, the vacuum valve 114, the sensor 108, the heater/cooler unit 102, and the vacuum source unit 112. In some embodiments, the filter 106 is configured to be detachably coupled to at least one of the tubing 104, the vacuum valve 114, the sensor 108, the heater/cooler unit 102, and the vacuum source unit 112. In some embodiments, at least one of the tubing 104, the filter 106, the vacuum source unit 112, the vacuum valve 114, and the sensor 108 is disposable, such that contamination from the disposable part(s) is discarded and build-up of contamination is prevented.

The filter 106 is fluidly coupled to the vacuum valve 114 by a first tube 104a and to the sensor 108 by a second tube 104b. The vacuum valve 114 is fluidly coupled to the vacuum source unit 112 by a third tube 104c and the sensor 108 is fluidly coupled to the internal space 102a (or the tank) of the heater/cooler unit 102 by a fourth tube 104d. In some embodiments, the vacuum source unit 112 is the house vacuum provided by the medical facility, such as through a wall vacuum socket. In some embodiments, the vacuum source unit 112 is a standalone, external vacuum source that can be provided with the system 100. In some embodiments, the fourth tube 104d is coupled to an existing overflow port 116 on the heater/cooler unit 102, where the existing overflow port 116 is provided for fluid overflow of one or more of the tanks in the heater/cooler unit 102. Connecting the fourth tube 104d to an existing overflow port 116 enables the system 100 to be retrofit to an existing heater/cooler unit 102.

The sensor 108 is configured to detect aerosols and/or contaminants, such as bacteria, in the tubing 104, suctioned from the internal space 102a (or the tank) of the heater/cooler unit 102. The sensor 108 is communicatively coupled to the vacuum valve 114 via communications path 118. In some embodiments, the sensor 108 is installed in the internal space 102a (or the tank) of the heater/cooler unit 102 (dashed arrow), such as in or near the overflow port 116 to sense or detect aerosols and/or contaminants in the internal space 102a (or the tank) of the heater/cooler unit 102.

The sensor 108 includes control electronics 120, such as a processor, configured to provide an output signal in response to detecting aerosols and/or contaminants. In some embodiments, the sensor 108 activates the vacuum valve 114 via the output signal to open the vacuum valve 114 and provide a vacuum or negative air pressure relative to the external air pressure from the vacuum source unit 112 to the filter 106 in response to detecting a contaminant or an aerosol. In some embodiments, the sensor 108 is configured to activate the vacuum valve 114 via the output signal to open the vacuum valve 114 for a limited time to provide the vacuum or negative air pressure relative to the external air pressure to the filter 106 in response to detecting a contaminant or an aerosol. In some embodiments, the sensor 108 is configured to activate the vacuum valve 114 via the output signal to open the vacuum valve 114 for less than 10 minutes to provide the vacuum or negative air pressure relative to the external air pressure to the filter 106 in response to detecting a contaminant or an aerosol. In some embodiments, the 
sensor 108 activates the vacuum valve 114 via the output signal for as long as an aerosol condition is detected. In some embodiments, the sensor 108 activates the vacuum valve 114 via the output signal for as long as an aerosol concentration exceeds an aerosol concentration threshold.

Figure 6:
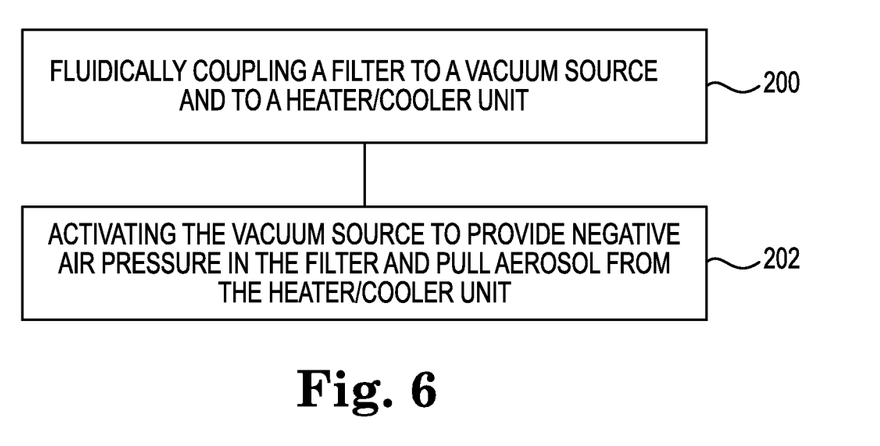
FIG. 6 is a diagram illustrating a method of eliminating and/or reducing aerosol emitted from a heater/cooler unit, according to embodiments of the disclosure.

In some embodiments, the sensor 108 activates an alarm or display on the sensor 108 via the output signal in response to detecting a contaminant or an aerosol. In some embodiments, the system 100 can be provided without a vacuum valve 114, such that the vacuum source 110 including the vacuum source unit 112 is manually activated to provide a vacuum or negative air pressure relative to the external air pressure to the filter 106, such as in response to an alarm or display on the sensor 108 indicating the presence of a contaminant, aerosols, or an aerosol concentration exceeding an aerosol concentration threshold.

In some embodiments, the system 100 can be provided without a vacuum valve 114 and the sensor 108 is communicatively coupled to the vacuum source unit 112 via communications path 122 (dashed line), such that the sensor 108 activates the vacuum source unit 112 directly to provide a vacuum or negative air pressure relative to the external air pressure to the filter 106 in response to sensing or detecting a contaminant, an aerosol, or an aerosol concentration. In some embodiments, the system 100 can be provided without a vacuum valve 114 and the sensor 108 is communicatively coupled to the vacuum source unit 112 via communications path 122 (dashed line), such that the sensor 108 activates the vacuum source unit 112 directly for a limited time to provide a vacuum or negative air pressure relative to the external air pressure to the filter 106 in response to sensing or detecting a contaminant or an aerosol. In some embodiments, the sensor 108 activates the vacuum source unit 112 directly to provide a vacuum or negative air pressure to the filter 106 for a duration defined by the time that the contaminant, aerosol, or aerosol concentration remains detected, i.e., for as long as an undesired sensed condition is detected.

In operation, the vacuum source 110 is activated to provide a vacuum or negative air pressure relative to the external air pressure to the filter 106. In some embodiments, the vacuum source 110 is activated via the sensor 108. In some embodiments, the vacuum source 110 is activated manually.

In some embodiments, the vacuum source 110 includes an electronic control unit 124, which is one or more of electronic control unit 124*a* in vacuum source unit 112 and electronic control unit 124*b* in vacuum valve 114. In some embodiments, the electronic control circuit 124 activates the vacuum source 110 for a limited time to remove the aerosol from the heater/cooler unit 102. In some embodiments, the electronic control circuit 124 activates the vacuum source 110 for a limited time when an operational condition of the heater/cooler unit 102 indicates a likelihood of aerosol production. In one embodiment, the operational condition indicating a likelihood of aerosol production includes activating a heating source within the heater/cooler unit 102. In some embodiments, the electronic control circuit 124 activates the vacuum source 110 when a contaminant aerosol, or aerosol concentration is detected for as long as the detection condition remains present. In some embodiments, the electronic control unit 124 is in communication with the heater/cooler unit 102, such as by a wire (not shown for clarity) or wireless communications. In some embodiments, the vacuum source 110 is turned on before the heater/cooler unit 102 is turned on. In some embodiments, the vacuum source 110 is turned on at the same time the heater/cooler unit 102 is turned on.

The filter 106 includes a filter container and the negative air pressure is provided to the filter container to suction aerosol from the heater/cooler unit 102 into the filter container. This eliminates and/or reduces the amount of aerosol that escapes from the heater/cooler unit 102 and the amount of aerosol that diffuses into the ambient air of the operating theatre. In some embodiments, the system 20 reduces the aerosol emitted from the heater/cooler unit 102 by at least 95%.

FIG. 6 is a diagram illustrating a method of reducing aerosol emitted from a heater/cooler unit, according to embodiments of the disclosure. Each of the systems described in this disclosure, including system 20 of FIG. 1 and system 100 of FIG. 5, can be used to provide the method.

At 200, the method includes fluidly coupling a filter to a vacuum source and to an internal space (or a tank) of a heater/cooler unit by using tubing. In some embodiments, the filter includes a hydrophobic filter configured to filter up to 99.99 percent of aerosolized micro-organisms and particulate matter in the aerosol received from the heater/cooler unit. In some embodiments, this coupling includes one or more tubes and/or devices coupled between the filter and each of the vacuum source and the heater cooler unit. In one embodiment, a sensor for detecting aerosol is provided in the tubing coupling the heater/cooler unit and the filter. In one embodiment, a vacuum valve is provided in the tubing coupling the vacuum source and the filter.

In some embodiments, portions of the systems 20 and 100 are disposable, where ease of attachment and detachment provides for easy disposability. In some embodiments, the tubing is detachably coupled, such that it is configured to be easily attached and detached, to one or more of the filter, the vacuum source, and the heater/cooler unit. In some embodiments, the filter is detachably coupled, such that it is configured to be easily attached and detached, to one or more of the tubing, the vacuum source, and the heater/cooler unit. In some embodiments, at least some of the tubing is disposable, such that at least some of the tubing can be disposed of to reduce contamination and build-up of contamination in the tubing. In some embodiments, the filter is disposable, such that the filter can be disposed of to reduce contamination and build-up of contamination in the filter. In some embodiments, a disposable unit is provided that includes the filter and tubing to couple the filter to each of the heater/cooler unit and the vacuum source. In a further embodiment, a disposable unit is provided that includes the filter, a vacuum source, and tubing to couple the filter to the heater/cooler unit. Optionally, additional tubing may be provided to couple the filter to the vacuum source.

Referring again to FIG. 6, at 202, the method includes activating the vacuum source for at least a limited time to provide negative air pressure relative to external air pressure in the filter to suction the aerosol from the internal space (or the tank) of the heater/cooler unit into the filter. In some embodiments, the aerosol emitted from the heater/cooler unit is eliminated. In some embodiments, the aerosol emitted from the heater/cooler unit is reduced by at least 95%.

In some embodiments (not shown in FIG. 6), the method includes sensing or detecting at least one of a contaminant such as bacteria, an aerosol, and an aerosol concentration, via a sensor. In one embodiment, the sensor is provided in the internal space (or the tank) of the heater/cooler unit. In one embodiment, the sensor is provided in the tubing coupling the heater/cooler and the filter. In some embodiments, the sensor can be configured to provide at least one of an alarm or display in response to the detecting of the at least one of the contaminant, the aerosol, and the aerosol concentration, and activating the vacuum source to provide a vacuum in response to the detecting of the at least one of the contaminant, aerosol, and aerosol concentration.

Figure 7:
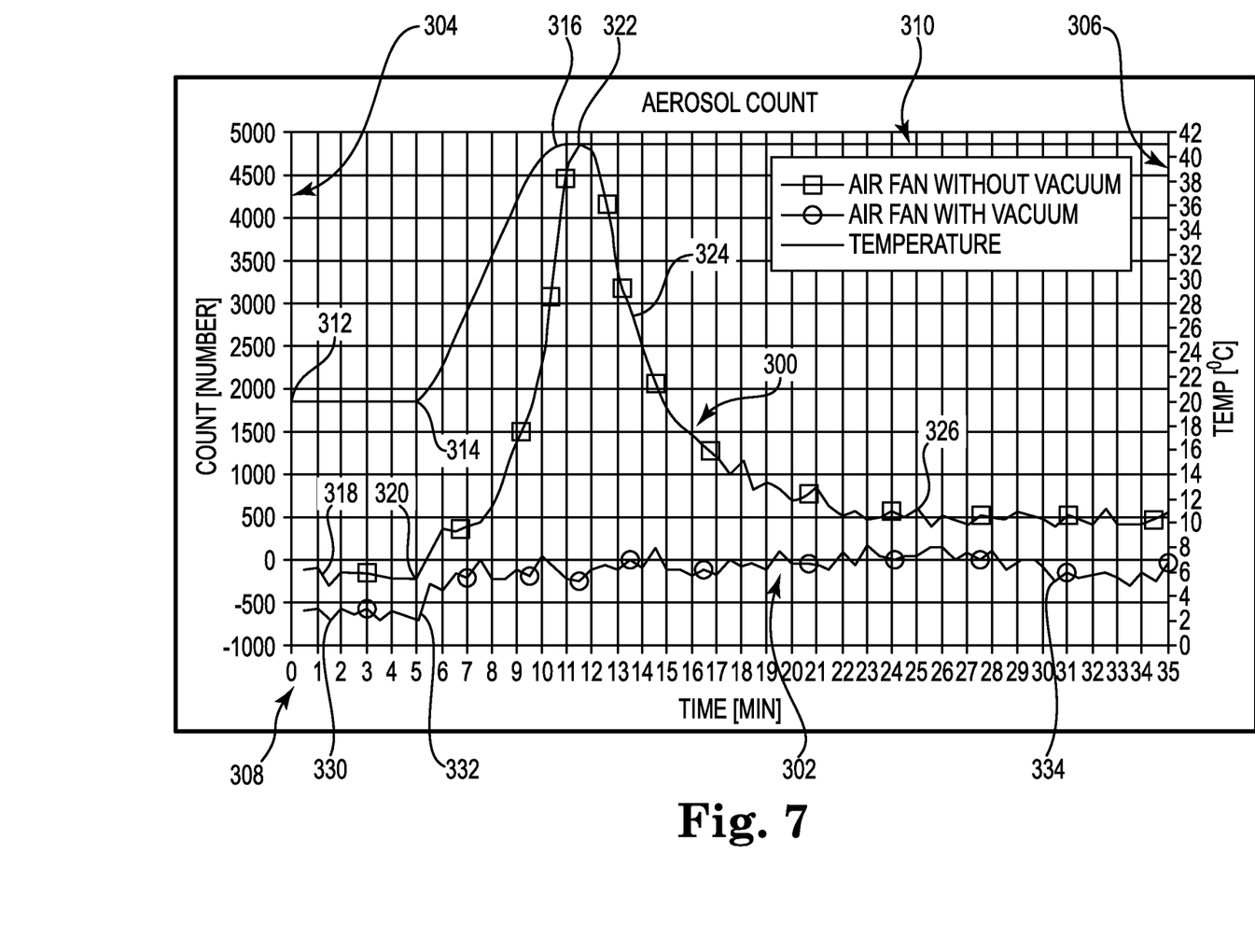
FIG. 7 is a graph illustrating aerosol particle count near the air fan over time for a heater/cooler system that does not include an aerosol elimination/reduction system described in this disclosure and for a heater/cooler system that does include an aerosol elimination/reduction system described in this disclosure.

FIG. 7 is a graph illustrating aerosol particle count near the air fan over time for a heater/cooler system that does not include an aerosol elimination/reduction system described in this disclosure (indicated at 300) and a heater/cooler system that does include an aerosol elimination/reduction system described in this disclosure (indicated at 302). The aerosol was measured near the fan of the heater/cooler unit to measure the maximum value expected for the aerosol dispersed into the operating room environment, but similar data could be obtained by measuring at different locations. The vertical axis at 304 depicts the aerosol particle count as reflected in lines 300 and 302). The temperature of the fluid in the heater/cooler unit is indicated at line 310, as reflected on vertical axis 306 in degrees centigrade (C). The horizontal axis at 308 depicts time in minutes. Aerosols are most heavily produced during the heater/cooler heating phase, where the temperature of the fluid in the heater/cooler unit is graphed at 310.

At 312, the heater/cooler unit has not yet started heating the heater/cooler fluid, which may be water, and the temperature of the fluid is about 20 C. At 314, at the five minute mark, the heater/cooler unit begins to heat the fluid from 20 C to about 41 C at 316, between the 10 and 11 minute marks. During this five to six minute heating time, the heater/cooler unit most heavily emits aerosols near the air fan.

The aerosol particle count measured in the air exiting the fan of the heater/cooler unit that does not have an attached aerosol reduction system 300 is at a particle count of about zero or below zero at 318. The particle count begins to increase almost immediately at 320, after the heater/cooler unit begins to heat the fluid at the five minute mark. The aerosol particle count increases to a maximum level of about 4800-4900 particles at 322, between the 11 and 12 minute marks. Thereafter, the particle count decreases at 324 to a relatively stable level of about 500 particles at 326, where it remains for the rest of the time.

In contrast, the aerosol particle count measured in the air exiting the fan of the heater/cooler unit that has an attached and activated aerosol reduction system is at a particle count of about −500 or below at 330. This particle count increases slightly at 332, to a particle count of about zero, which is about the same as the initial particle count measured in the air exiting the fan of the heater/cooler unit that does not have an attached aerosol reduction system at 318. Thereafter, the particle count remains at about zero for the remainder of the time, decreasing slightly at the 30 minute mark at 334.

The difference in the graph of the aerosol particle count emitted by the heater/cooler system that does not include an aerosol reduction system (line 300) and the graph of the aerosol particle count emitted by the heater/cooler system that does include an aerosol reduction system (line 302), exemplifies the improvement achieved by the aerosol reduction system described in this disclosure.

Figure 8:
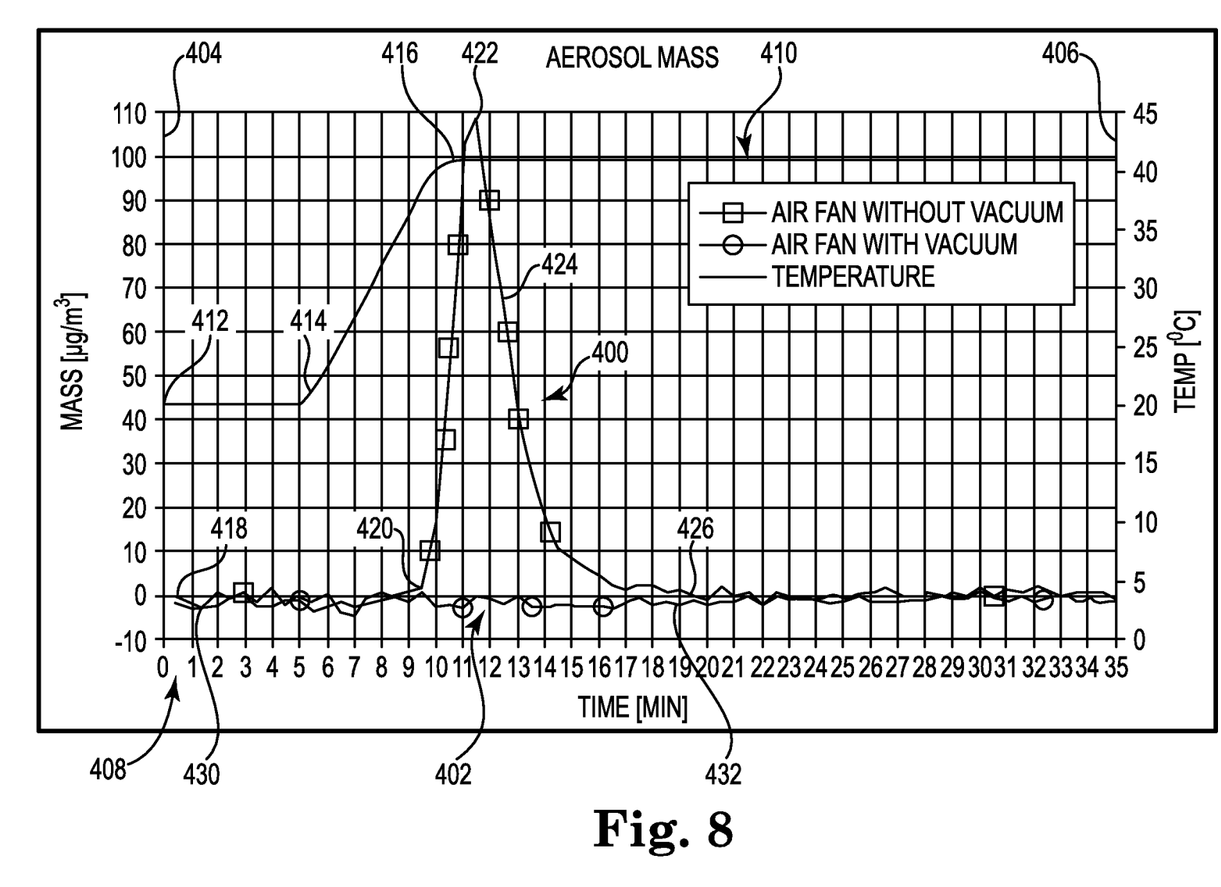
FIG. 8 is a graph illustrating aerosol particle mass near the air fan over time for a heater/cooler system that does not include an aerosol elimination/reduction system described in this disclosure and for a heater/cooler system that does include an aerosol elimination/reduction system described in this disclosure.

FIG. 8 is a graph illustrating aerosol particle mass near the air fan over time for a heater/cooler system that does not include an aerosol elimination/reduction system described in this disclosure (line 400) and a heater/cooler system that does include an aerosol elimination/reduction system described in this disclosure (line 402). The aerosol was measured near the fan of the heater/cooler unit to measure the maximum value expected for the aerosol dispersed into the operating room environment, but similar data could be obtained by measuring at different locations. The vertical axis at 404 depicts the aerosol particle mass in micrograms per meter cubed (ug/m3). The temperature of the fluid in the heater/cooler unit is indicated at line 410, as reflected on the vertical axis at 406 in degrees centigrade (C). The horizontal axis at 408 depicts time in minutes. Aerosols are most heavily produced during the heater/cooler heating phase, where the temperature of the fluid in the heater/cooler unit is graphed at line 410.

At 412, the heater/cooler unit has not yet started heating the heater/cooler fluid, which may be water, and the temperature of the fluid is about 20 C. At 414, at the five minute mark, the heater/cooler unit begins to heat the fluid from 20 C to about 41 C at 416, between the 10 and 11 minute marks. During this five to six minute heating time, the heater/cooler unit most heavily emits aerosols into the air.

The aerosol particle mass in the air exiting the fan of the heater/cooler unit that does not have an attached aerosol reduction system is at a particle mass of about zero at 418. The particle mass begins to increase at 420 at the nine and a half minute mark, after the heater/cooler unit begins to heat the fluid at the five minute mark. The aerosol particle mass increases to a maximum level of about 110 at 422 between the 11 and 12 minute marks. Thereafter, the particle mass decreases at 424 to a relatively stable level of about zero at 426, where it remains for the rest of the time.

In contrast, the aerosol particle mass in the air exiting the fan of the heater/cooler unit that has an attached and activated aerosol reduction system is at a particle mass of about zero at 430 and remains at about zero for the remainder of the time at 432.

The difference in the graph of the aerosol particle mass emitted by the heater/cooler system that does not include an aerosol reduction system (line 400) and the graph of the aerosol particle mass emitted by the heater/cooler system that does include an aerosol reduction system (line 402), exemplifies the improvement achieved by the aerosol reduction system described in this disclosure.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. A disposable system for eliminating or reducing aerosol emitted from an enclosed heater/cooler unit, the heater/cooler unit including an enclosure, the enclosure containing a heater and an internal space that contains at least one fluid tank therein, the system comprising:

a filter unit including a filter container, a filter cap, and a hydrophobic antibacterial filter element, the filter unit separate from and outside the enclosure of the enclosed heater/cooler unit, the filter cap configured to be attached to the filter container in an airtight connection, the filter cap having a first connection port and a second connection port;

a first tubing for connecting the first connection port on the filter cap to the enclosure of the heater/cooler unit and fluidly coupling the internal space of the heater/cooler unit to the filter unit;

a second tubing for connecting to the second connection port on the filter cap and fluidly coupling the filter unit to a vacuum source;

wherein the hydrophobic antibacterial filter element includes first and second separate hydrophobic antibacterial filter stages including a first hydrophobic antibacterial filter stage coupled to the first connection port and a second hydrophobic antibacterial filter stage coupled to the second connection port;

wherein, during at least a portion of the operation of the heater/cooler unit, the vacuum source creates a negative air pressure in the filter container, such that an aerosol in the internal space of the heater/cooler unit is suctioned into the container and filtered by the hydrophobic antibacterial filter element.

2. The system of claim 1, wherein the system substantially eliminates the aerosol emitted from the heater/cooler unit.

3. The system of claim 1, wherein the hydrophobic antibacterial filter is configured to filter up to 99.99 percent of aerosolized micro-organisms and particulate matter in the aerosol received from the heater/cooler unit.

4. A disposable system for eliminating or reducing aerosol emitted from an enclosed heater/cooler unit, the heater/cooler unit including an enclosure, the enclosure containing a heater and an internal space that contains at least one fluid tank therein, the system comprising:
a filter unit including a filter container and a hydrophobic antibacterial filter element, the filter unit separate from and outside the enclosure of the enclosed heater/cooler unit, wherein the hydrophobic antibacterial filter element includes a hydrophobic filter stage, a pre-filter stage, and a breathing screen disposed between and separating the hydrophobic filter stage and the pre-filter stage;
a first tubing for connecting the filter unit to the enclosure of the heater/cooler unit and fluidly coupling the internal space of the heater/cooler unit to the filter unit; and
a second tubing for connecting to the filter unit and fluidly coupling the filter unit to a vacuum source;
wherein, during at least a portion of the operation of the heater/cooler unit, the vacuum source creates a negative air pressure in the filter container, such that an aerosol in the internal space of the heater/cooler unit is suctioned into the container and filtered by the antibacterial filter element.

5. The system of claim 1, wherein the tubing is configured to be detachable from at least one of the heater/cooler unit and the vacuum source, and the tubing is configured to be disposable such that contamination from the tubing is discarded and build-up of contamination is prevented.

6. The system of claim 1, wherein the filter unit is configured to be detachable from at least one of the tubing, the heater/cooler unit, and the vacuum source, wherein the filter unit is configured to be disposable to discard contamination from the filter and prevent build-up of contamination.

7. The system of claim 1 further comprising a sensor configured to detect at least one of an aerosol, an aerosol concentration, and a contaminant.

8. The system of claim 7, wherein the sensor is configured to provide an alarm in response to detection of at least one of the aerosol, the aerosol concentration, and the contaminant.

9. The system of claim 7, wherein the sensor is configured to activate the vacuum source to provide the negative pressure in the filter container in response to the sensor detecting the at least one of the aerosol, the aerosol concentration, and the contaminant.

10. The system of claim 1 further comprising a valve fluidly coupled to the first tube and to the vacuum source.

11. The system of claim 1, wherein the vacuum source is a stand-alone external vacuum source.

12. The system of claim 1, further comprising a disposable vacuum unit coupled to the second tubing to provide the vacuum source.

13. The system of claim 1, wherein the first tubing is configured to be detachable from the heater/cooler unit, the second tubing is configured to be detachable from the vacuum source, and the tubing and filter unit are disposable such that contamination from the tubing and filter unit are discarded and build-up of contamination is prevented.

14. A disposable system for eliminating or reducing aerosol emitted from a heater/cooler unit, the heater/cooler unit containing a heater, an internal space that contains a fluid tank therein, and an overflow port fluidly coupled to the internal space, the system comprising:
tubing including a first tube and a second tube;
a vacuum source; and
a filter fluidly coupled to the vacuum source by the first tube and configured to be fluidly coupled to a heater/cooler unit by the second tube, the filter including a hydrophobic antibacterial filter element including a hydrophobic filter stage, a pre-filter stage, and a breathing screen disposed between and separating the hydrophobic filter stage and the pre-filter stage, wherein the vacuum source provides negative air pressure to the filter to suction aerosol from the internal space of the heater/cooler unit to the filter.

15. The system of claim 14, wherein the vacuum source includes a valve fluidly coupled to the tubing and to the vacuum source.

16. The system of claim 14, wherein the vacuum source is a non-disposable vacuum source.

17. The system of claim 14, wherein the vacuum source is configured to be activated for a limited time before or concurrently with activation of the heater.

18. The system of claim 17, wherein the vacuum source is configured to be activated for at least 10 minutes.

19. The system of claim 14, comprising a sensor configured to detect at least one of an aerosol, an aerosol concentration, and a contaminant.

20. The system of claim 19, wherein the sensor is configured to provide an alarm in response to detecting the at least one of the aerosol, the aerosol concentration, and the contaminant.

21. The system of claim 19, wherein the sensor is configured to activate the vacuum source and provide a vacuum in response to the sensor detecting the at least one of the aerosol, aerosol concentration exceeding an aerosol threshold, and the contaminant.

22. A method of eliminating or reducing aerosol emitted from a heater/cooler unit operable during a surgical procedure on a patient, the heater/cooler unit containing a heater, an internal space that contains a fluid tank therein, and an overflow port, comprising:
connecting a filter to a vacuum source and to the overflow port of the heater/cooler unit by tubing, the filter including a hydrophobic antibacterial filter element with a hydrophobic filter stage, a pre-filter stage, and a breathing screen disposed between and separating the hydrophobic filter stage and the pre-filter stage;
activating the vacuum source for at least a limited time during at least a portion of an operation of the heater to provide negative air pressure in the filter and suction aerosol from the internal space of the heater/cooler unit into the filter;

disconnecting the filter and tubing from the vacuum source and the overflow port after completion of the surgical procedure; and disposing of the filter and tubing.

23. The method of claim 22, wherein the aerosol emitted from the heater/cooler unit is reduced by at least 95%.

* * * * *